US006621031B2

(12) United States Patent
Stevens

(10) Patent No.: US 6,621,031 B2
(45) Date of Patent: Sep. 16, 2003

(54) SYRINGE AND NEEDLE DESTRUCTION DEVICE

(76) Inventor: Carlile R. Stevens, 4119 Hwy. 2147, Suite 6, Marble Falls, TX (US) 78654

( * ) Notice: Subject to any disclaimer, the term of this patent is extended or adjusted under 35 U.S.C. 154(b) by 0 days.

(21) Appl. No.: 10/103,051

(22) Filed: Mar. 20, 2002

(65) Prior Publication Data

US 2002/0144896 A1 Oct. 10, 2002

Related U.S. Application Data

(60) Provisional application No. 60/281,840, filed on Apr. 6, 2001.

(51) Int. Cl.[7] ........................ B23K 9/013; A61G 12/00; A61L 11/00

(52) U.S. Cl. ........................ 219/69.1; 110/250; 219/68; 219/384

(58) Field of Search ......................... 219/68, 69.1, 383, 219/384; 110/250

(56) References Cited

U.S. PATENT DOCUMENTS 5,276,297 A * 1/1994 Nara ........................... 219/68
5,710,404 A * 1/1998 Descent ....................... 219/68
6,384,362 B1 * 5/2002 Adkins ...................... 219/69.1

FOREIGN PATENT DOCUMENTS

| | | | |
|---|---|---|---|
| FR | 2686516 A1 | * | 7/1993 |
| FR | 2698273 A1 | * | 5/1994 |
| JP | 6-245987 A | * | 9/1994 |
| JP | 7-303677 A | * | 11/1995 |
| JP | 11-33065 A | * | 2/1999 |

* cited by examiner

*Primary Examiner*—Geoffrey S. Evans
(74) *Attorney, Agent, or Firm*—Roger A. Marrs

(57) ABSTRACT

A device that operates to reduce the hazard involved in the disposal of conventional hypodermic needles used throughout the medical world. When the needle is presented to the inventive device, while still attached to the syringe, it is vaporized an electric arc with its final connection point to the syringe sterilized. In a second embodiment of the device, the entire syringe, including the needle, is vaporized by an electric arc transferred between electrodes. The byproducts of the needle destruction process are sterile metal vapor such as iron oxide, water vapor and carbon dioxide. The heat is so intense that all organic compounds present within the needle are reduced to their basic elements of hydrogen, oxygen and carbon with trace amount of nitrogen and infinitesimal amounts of other trace elements. When the entire syringe is destroyed, all organic compounds of the plastic are reduced to the basic elements.

8 Claims, 2 Drawing Sheets

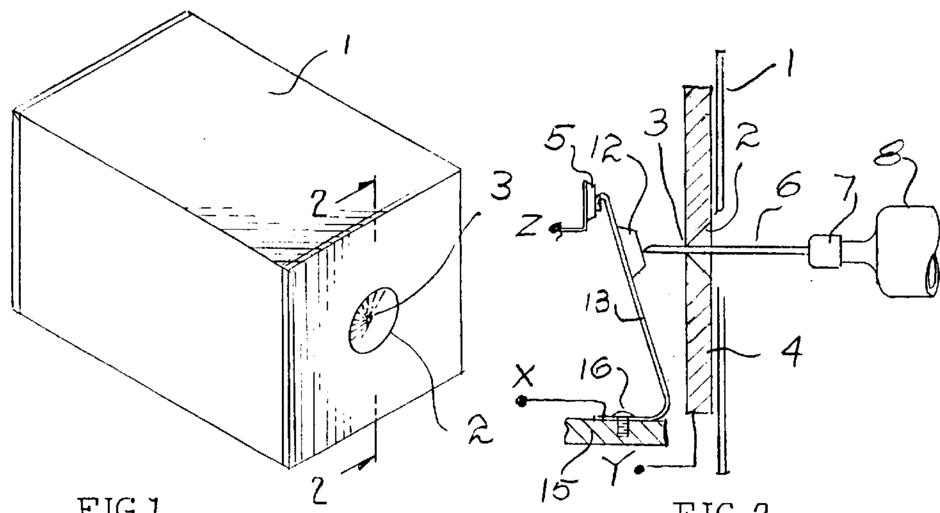
FIG. 1.
FIG. 2.
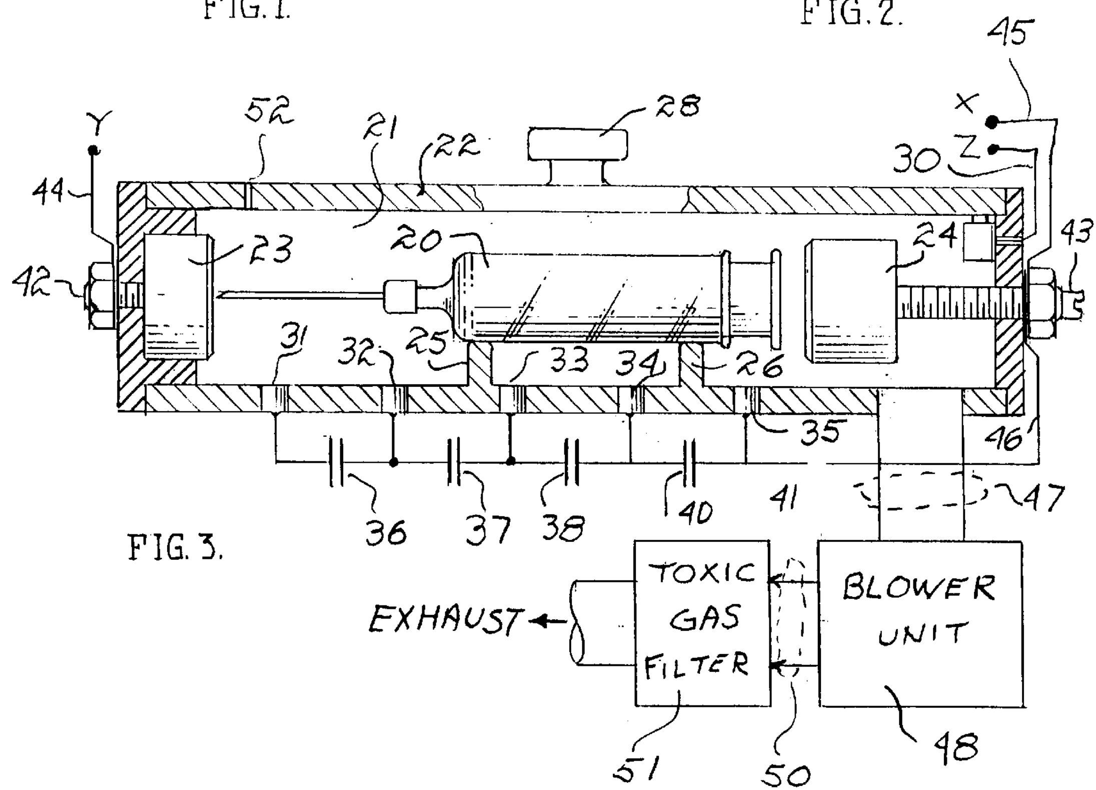
FIG. 3.
TOXIC GAS FILTER
BLOWER UNIT
EXHAUST

SYRINGE AND NEEDLE DESTRUCTION DEVICE

This application claim benefit to provisional application 60/281,840 Apr. 6, 2001.

BACKGROUND OF THE INVENTION

1. Field of the Invention

The invention disclosed herein involves the establishment of an electric arc with either a hypodermic needle or a complete syringe suspended within said arc and, thus, vaporized by the heat of that arc. With the needle only destroyer version, the needle is placed such that one end is in contact with a heavy heat absorbent electrode. The second electrode is positioned at the end of the needle, such that it does not actually make contact with the needle. A high voltage establishes an arc between this second electrode and the needle, which acts as a conductive path for high current to form a plasma spot of intense heat forming a plasma spot which rapidly transfers the length of the needle until the needle is entirely consumed.

2. Brief Description of the Prior Art

There are a number of needle destroyers or needle storage techniques that are utilized by the medical industry. Presently, the primary method of needle disposal involves placing the needle, after first removing it from the syringe, in a box and disposing of the syringe in the conventional red bag. The box is designed to contain the needles and prevent any accidental punctures to those who are involved with disposing of the boxes. However accidental punctures are known to occur and the needles with the box are not sterile and can contaminate anybody accidentally coming into contact with them. Safe disposal of the boxes has become a major problem. Other methods of disposal involve cutting off, rather than removing, the needle from the syringe such that only one hand is required. In some cases, the syringe with the needle still attached are disposed of together in a special container but something still must be done with the container. Other forms of needle destruction are being considered for the market which involve heating or melting the needle with an electric current until it becomes soft with motor driven electrodes to maintain needle contact while the current is passed through it, causing it to melt. Although the heat from this process most likely sterilizes the needle, it is an expensive, clumsy method and requires continuous maintenance.

SUMMARY OF THE INVENTION

Accordingly, the above problems and difficulties are avoided by the present invention which provides a syringe and/or needle destruction device having a housing, enclosing a pair of electrodes and an insertion port provided through the housing and one electrode for insertably receiving a needle. The other electrode is spring biased and includes a ceramic button separating direct engagement of the needle with the other electrode. A contact is connected with the other electrode when pivoting occurs to complete an electrical circuit. Since the needle is part of the circuit, high voltage and current will destroy and vaporize the needle.

In another embodiment, a syringe and needle combination are placed in an enclosure and the electrical circuit is employed to destroy and vaporize the combination. A blower unit and toxic gas filter are employed to clear the enclosure of toxic and non-toxic fumes.

The primary object of the subject invention is the total destruction of hypodermic needles and the like immediately after their use, such that containment, storage and transfer to another location for destruction or disposal would not be required.

A second object of this invention is to sterilize at least to the point at which the needle was connected to the syringe or other medical instruments, such as in a IV tube or the like.

Yet another object of the invention is to be able to expand the amount of energy to destroy the entire needle and syringe.

A further object of the invention is to totally sterilize the resultant by products of this destruction.

Still a further object of the invention is to accomplish all of the above in a safe and non-disruptive manner.

Another object of the invention is to accomplish all of the above objects with a relatively small device.

The final object of the invention is to accomplish all the other objects in such an economical manner as to make its application practical throughout the entire medical industry.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a perspective view of a syringe and needle destruction device incorporating the present invention;

FIG. 2 is a sectional view of the device shown in FIG. 1 illustrating a contaminated needle in position for destruction;

FIG. 3 is an enlarged longitudinal sectional view of the device for destroying both a needle and syringe.

DESCRIPTION OF PREFERRED EMBODIMENT

Figure 4:
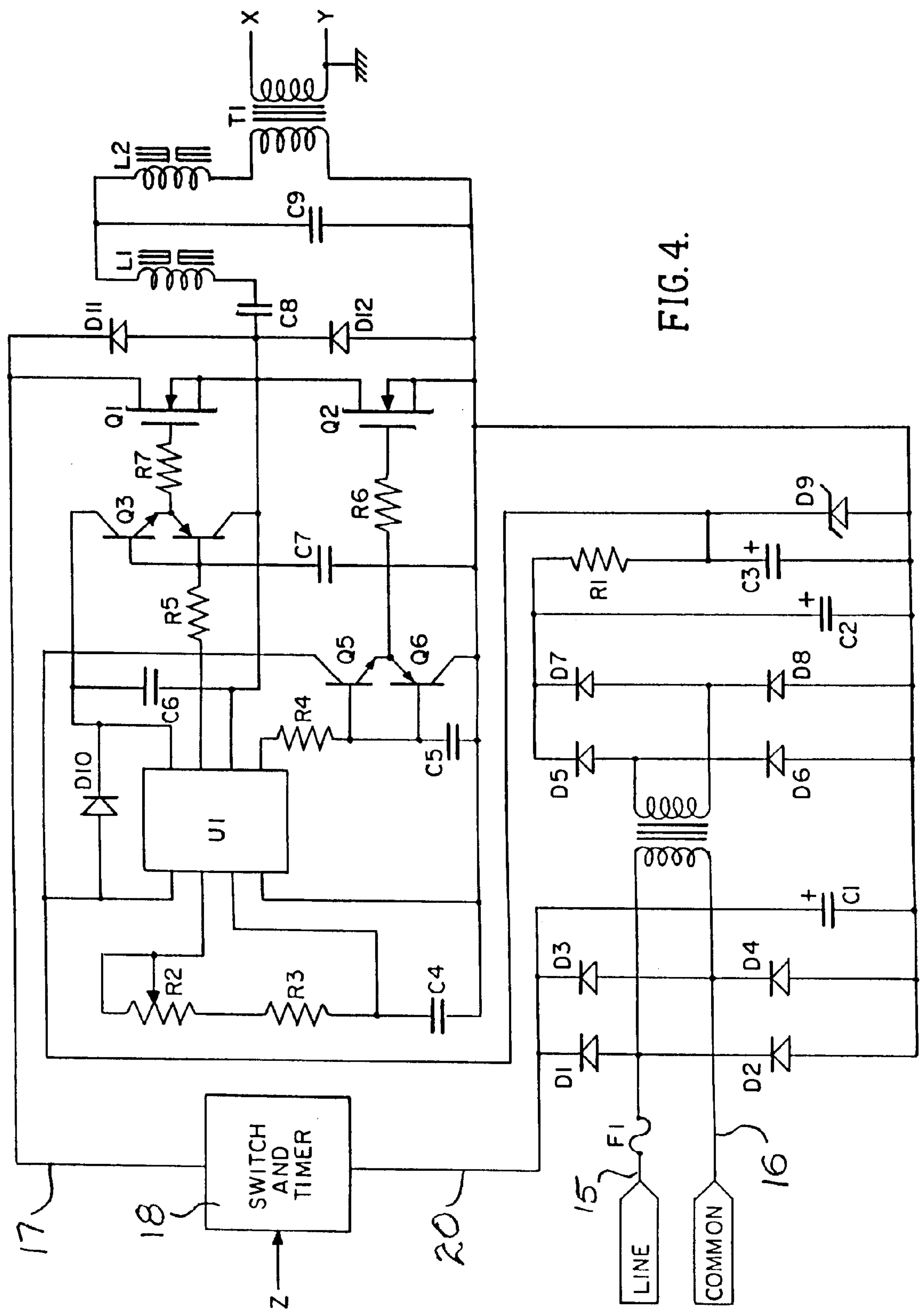
FIG. 4 is a circuit diagram for supplying high voltage and high current to establish connection and high current to sustain an arc and vaporize the needle.

FIG. 1 shows a needle destroying module 1 having a cone-shaped hole with a large outer diameter 2 and a small inner diameter 3. A person holding a used needle and syringe presents the needle to the cone-shaped hole and the outer diameter guides the needle into the small hole 3 so that it may enter the interior of module 1 and be destroyed.

FIG. 2 shows the same shaped hole outer dimension 2 and inner dimension 3 in a cross sectional view with an electrode 4 and a needle 6 protruding through said hole. The needle 6 is attached to a header 7 which is attached to syringe 8. When needle 6 enters the hole 3, it comes in contact with a ceramic button 12 attached to a spring electrode 13. The electrode 13 and button 12 are shown in a relaxed position in broken lines. When the needle is fully inserted into the device as shown, the needle header comes in contact with electrode 4 and the needle pushes electrode 13 which engages against contact 5 to turn the device "on", as will be discussed in FIG. 3. A straight contact with electrode 13 would simply short the output. In order for an arc to be established, ceramic button 12 is inserted between the electrode and the needle, and this allows an arc to form between the needle and electrode 13 causing current to pass through the needle and into electrode 4. The arc current is connected to a power supply through lines 14 and 11 to point X and Y. Electrode 4 pivots at point 10 which allows it to make contact with a contact 5, which is connected to a power supply at point Z. Once the arc has been established, the needle will be consumed from the tip backwards towards the syringe. As this happens, spring electrode 13 which is anchored by a screw 16 to a block 15 will spring towards the syringe, causing the arc to be maintained and the needle to be consumed. When the burning is complete, there will be a tiny, melted and sealed stub of metal at the needle holder 7. At this point, the syringe 8 is withdrawn and safely disposed of.

Referring to FIG. 3, which is a cross-sectional view of the inventive device as it would be employed to destroy the entire needle and syringe, a syringe 20, with used needle attached, is placed in chamber 21 by lifting lid 22 and resting the syringe and needle between electrodes 23 and 24 on supports 25 and 26. Lid 22 is then closed using handle 28 causing it to press down and activate a switch 27. Closing switch 27 causes a signal to connect via line 30 to a power supply module of FIG. 4 at point Z to start the syringe and needle destruction process. The destruction process is started by applying a high voltage between electrodes 23 and 24 via mounting screws 42 and 43, lines 44 and 45 to points X and Y of FIG. 4 respectively. Electrodes 31–35 in combination with capacitors 36–41 act to enable a plasma arc to travel the full length of chamber 21. When the voltage is first applied there is no current flowing and therefore no voltage drop across the capacitive reactance of capacitors 36–41 so the same voltage appears at electrodes 31–35 as is present on electrode 24. This causes an arc to form between the electrode 23, the needle and the closest electrode 31. Once the arc is formed and the current starts to flow, there is a voltage drop across capacitors 36–41. The values of these capacitors are selected such that the major voltage drop is across capacitor 36. This causes the arc to transfer to electrode 32. Again the selection of values for the capacitors causes the major drop now to be across capacitor 37. In this manner, the arc is established down the chamber until it is between electrodes 23 and 24. Once the arc plasma path has been established, its impedance is very low and electrodes 31–35 will no longer be involved. In some cases, depending on the size of the needle, syringe and chamber it may operate better to place capacitors 36–41 in parallel with each connected to its respective electrode 31–35 and electrode 24. Since electrodes 23 and 24 have a large heat sinking capability and are highly conductive, they will not be consumed along with the needle and syringe.

At the same time, the voltage is applied, the blower unit 48 is activated drawing air from chamber 21 via duct 47. Air can enter chamber 21 only through a pinhole 52, thus the strong suction of the blower unit substantially lowers the pressure in chamber 21 which facilitates the formation of the arc plasma. Once the plasma is formed, large amounts of gasses are produced which forms the breakdown of the plastic material of the syringe. Depending upon the type plastic used, there is a possibility that some of this gas might be toxic; thus, the output of the blower unit is connected to a toxic gas filter 51 through duct 50. Normally the heat is so intense that everything is reduced to non-toxic byproducts. Once everything has been destroyed, chamber 21 is cleared of all gasses by the air flowing in through pinhole 52.

Referring now to FIG. 4, line power enters on line and common inputs 15 and 16 which is protected by fuse F1, and is rectified to Direct Current power by bridge diodes comprising D1, D2, D3 and D4 and filter capacitor C1. Input power is also fed to a primary transformer T2, the output of which is rectified by bridge diodes 5, 6, 7 and 8, filtered by capacitor C2 and regulated by a zener diode D9 to supply drive to the oscillating circuit.

Contact with point 5 of FIG. 4, which is connected to point Z, detects the presence of the needle and turns on timer and switch 18, which connects the power from the input bridge rectifier on line 17 to power FET Q1, which is connected in half bridge configuration with power FET Q2. Diodes D11 and D12 across Q1 and Q2 respectively are added for protection, since even though FET transistors have these diodes built-in they are not often of high enough quality to provide the protection needed when working with high frequency arcs. IC chip U1 supplies the high frequency drive for the output. The frequency is set by the value of capacitor C4 and the adjustment of variable resistor R2. Resistor R3 is provided to set the proper frequency limit. IC chip U1 provides a high side driver of driving the top transistor for the bridge configuration, since Q1 and Q2 are high power FETS, the drive from U1 needs to be augmented by complimentary emitter follower pairs Q3 and Q4 in the case of Q1 and Q5 and Q6 in the case of Q2. Resistor R5 and C7 in the case of the drive for Q1 and R4 and C5 in the case of the drive for Q2 form a slight slowdown of the switching to eliminate radio frequency interference when the needle is arcing as well as providing a filter to prevent high frequency spikes from getting into the fairly sensitive U1 chip. The power to operate the high side driver comes from the action of diode D10 and capacitor C6. When Q2 is "on", capacitor C6 is charged to the logic supply voltage through diode D10. When Q1 is on, capacitor C6 is connected to its source at the bottom, thus the supply voltage will always be maintained at the logic supply voltage plus the output voltage of the junction of Q1 and Q2.

Capacitor C8 serves as a DC blocking capacitor allowing only the high frequency AC to pass from the half bridge to L1, C9, L2, and output transformer T1. The values of L1, L2, capacitor C9 and the turns ratio of transformer T1 are set when there is no needle present and the appropriate frequency is applied through C8. The resonance effect of L1 and C9 produce a slightly stepped up voltage at the primary of T1, and since no current is flowing at this time, there will be a drop across inductor L2 and maximum output voltage will be achieved which is enough to establish an arc. Once the arc is established, the impedance of the primary of T1 becomes very low, and the current flowing into the transformer and into the needle is limited by the value of inductor L2. All these values are selected carefully such that maximum current and power can be transferred into the arc when the needle is present and maximum voltage can be achieved when the needle is absent.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A medical instrument destruction and vaporizing device comprising:

a housing having an opening;

a pair of electrodes disposed in said housing in spaced-apart relationship;

a selected electrode of said pair resiliently biased towards said non-selected electrode of said pair;

said selected electrode being elongated with one fixed end thereof secured to said housing and an opposite end terminating in a terminal;

a stationary contact disposed in said housing in fixed spaced-apart relationship with respect to said non-selected electrode;

an insulative button carried on said selected electrode midway between opposite ends thereof in alignment with said housing opening so as to be forcibly engaged by a needle projecting into and through said housing opening; and electrical circuit means operably connected between said electrodes to provide a high current to form a plasma spot of intense heat transferring to the needle for complete vaporization and destruction.

2. The device defined in claim 1 wherein:

said button is composed of a ceramic material secured to said selected electrode.

3. The device defined in claim 2 wherein:

said non-selected electrode and said housing are provided with coaxial and coextensive openings having tapered sidewalls diverting into a common aperture adapted to conduct the needle therethrough.

4. A medical instrument destruction and vaporizing device comprising:

a housing;

means in said housing for receiving an implement to be vaporized and destroyed;

a pair of electrodes disposed in said housing separated by the implement to be vaporized and destroyed; and an electrical circuit operably coupled to said electrodes for generating a high voltage arc forming a conductive path for high current to create a plasma spot traveling along the implement while simultaneously vaporizing said implement.

5. The device defined in claim 4 including:

a blower unit connected to said housing for exhausting said housing of gases resulting from vaporization of the implement.

6. The device defined in claim 5 including:

a toxic gas filter coupled to said blower unit for receiving and cleansing exhausted gases.

7. The device defined in claim 6 including:

support means in said housing for holding the implement between said electrodes.

8. The device defined in claim 7 including:

an electronic circuit coupled between said electrodes creating current to provide an arc; and said electrodes are arranged in a linear row along the length of the implement and are sequentially energized so that said arc travels along the length of the implement.

* * * * *